(12) United States Patent
Tearney et al.

(10) Patent No.: US 6,282,011 B1
(45) Date of Patent: Aug. 28, 2001

(54) GRATING BASED PHASE CONTROL OPTICAL DELAY LINE

(75) Inventors: Guillermo Tearney, Cambridge; Brett E. Bouma, Boston; James G. Fujimoto, Cambridge, all of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/603,806

(22) Filed: Jun. 26, 2000

Related U.S. Application Data

(60) Division of application No. 09/079,687, filed on May 15, 1998, now Pat. No. 6,111,645, and a continuation-in-part of application No. 08/607,787, filed on Feb. 27, 1996, which is a continuation-in-part of application No. 08/577,366, filed on Dec. 22, 1995, now Pat. No. 5,748,598, and a continuation-in-part of application No. 08/252,940, filed on Jun. 2, 1994, now abandoned, said application No. 09/079,687, is a continuation-in-part of application No. 08/916,759, filed on Aug. 19, 1997, now Pat. No. 5,784,352, which is a continuation of application No. 08/492,738, filed on Jun. 21, 1997, now abandoned, which is a continuation-in-part of application No. 08/033,194, filed on Mar. 16, 1993, now Pat. No. 5,459,570, which is a continuation of application No. 07/692,877, filed on Apr. 29, 1991, now abandoned.

(60) Provisional application No. 60/046,739, filed on May 16, 1997.

(51) Int. Cl.⁷ ....................................................... G02F 1/11
(52) U.S. Cl. .......................... 359/287; 359/331; 359/285; 356/450; 356/484; 356/485; 250/227.27
(58) Field of Search ......................... 250/227.12, 227.27; 356/450, 477, 479, 484, 485, 488, 496, 497, 197, 205, 285, 287, 331, 566, 578, 583

(56) References Cited

U.S. PATENT DOCUMENTS 3,549,239  12/1970  Brienza et al. ...................... 359/566
3,961,841   6/1976  Giordmaine .......................... 359/264
5,032,722   7/1991  Boesl et al. .......................... 250/287

(List continued on next page.)

FOREIGN PATENT DOCUMENTS 35 27 245    2/1987   (DE) ............................................ 11/2
4309056      9/1994   (DE) .
2 191 855   12/1987   (GB) ........................................ 21/84
6-35946      5/1994   (JP) .
92/19930    11/1992   (WO) .
WO 92/19930 11/1992   (WO) .

OTHER PUBLICATIONS

Bail, M. et al. "Optical coherence tomography by 'spectral radar' for the analysis of human skin," *The International Society for Optical Engineering*, vol. 3196, 1997.

(List continued on next page.)

*Primary Examiner*—Georgia Epps
*Assistant Examiner*—David N. Spector
(74) *Attorney, Agent, or Firm*—Testa, Hurwitz & Thibeault, LLP

(57) ABSTRACT

An apparatus for performing high speed scanning of an optical delay and its application for performing optical interferometry, ranging, and imaging, including cross sectional imaging using optical coherence tomography, is disclosed. The apparatus achieves optical delay scanning by using diffractive optical elements in conjunction with imaging optics. In one embodiment a diffraction grating disperses an optical beam into different spectral frequency or wavelength components which are collimated by a lens. A mirror is placed one focal length away from the lens and the alteration of the grating groove density, the grating input angle, the grating output angle, and/or the mirror tilt produce a change in optical group and phase delay. This apparatus permits the optical group and phase delay to be scanned by scanning the angle of the mirror. In other embodiments, this device permits optical delay scanning without the use of moving parts.

10 Claims, 13 Drawing Sheets

U.S. PATENT DOCUMENTS

| | | | |
|---|---|---|---|
| 5,202,745 | 4/1993 | Sorin et al. | 600/504 |
| 5,383,467 | 1/1995 | Auer et al. | 600/342 |
| 5,459,570 | 10/1995 | Swanson et al. | 356/479 |
| 5,465,147 | 11/1995 | Swanson | 356/497 |
| 5,501,226 | 3/1996 | Petersen et al. | 600/504 |
| 5,555,087 | 9/1996 | Miyagawa et al. | 356/485 |
| 6,111,645 * | 8/2000 | Tearney et al. | 356/354 |
| 6,160,826 * | 12/2000 | Swanson et al. | 372/20 |

OTHER PUBLICATIONS

Chinn et al. "Optical coherence tomography using a frequency–tunable optical source," *Optics Letters*, vol. 22, No. 5, 1997, pp. 340–347.

Dickensheets et al. "Micromachined scanning confocal optical microscope," *Optics Letters*, vol. 21, No. 10, 1996, pp. 764–766.

Edelstein, D.C. et al. "Rapid programmable 300 ps optical delay scanner and signal–averaging system for ultrafast measurements," *Rev. Sci. Instrum*, vol. 62, No. 3, 1991, pp. 579–583.

Eigensee, A. et al. "A new method of short–coherence–interferometry in human skin (in vivo) and in solid volume scatterers," *European Biomedical Optics IBIOS96 Week*, Vienna, Austria, pp. 1–10.

Fercher, Adolf F., "Optical Coherence Tomography," *Journal of Biomedical Optics*, vol. 1, No. 2, 1996, pp. 157–173.

Heritage, J. P. et al. "Picosecond pulse shaping by spectral phase and amplitude manipulation," *Optics Letter*, vol. 10, No. 12, 1985, pp. 609–611.

Hillegas, C. W. et al. "Femtosecond laser pulse shaping by use of microsecond radio–frequency pulses," *Optics Letter*, vol. 19, No. 10, 1994, pp. 737–739.

Huang, David et al. "Optical Coherence Tomography," *Science*, vol. 254, 1991, pp. 1178–1181.

Gmitro, Arthur et al. "Confocal microscopy through a fiber–optic imaging bundle," *Optics Letters*, vol. 18, No. 8, 1993, pp. 565–567.

Kwong, K.F. et al. "400–Hz mechanical scanning optical delay line," *Optics Letters*, vol. 18, No. 7, 1993, pp. 558–560.

Martinez, Oscar E. 3000 Times Grating Compressor with Positive Group Velocity Dispersion: Application to Fiber Compensation in 1.3–1.6 $\mu$m Region, *IEEE Journal of Quantum Electronics*, vol. QE–23, No. 1, 1987, pp. 59–64.

Ng, Kok–Hwee, MSEE et al. Arterial Imaging With a New Forward–Viewing Intravascular Ultrasound Catheter, II Three–Dimensional Reconstruction and Display of Data, *Circulation*, vol. 89, No. 2, 1994, pp. 718–723.

Park, Heungsup et al. "High resolution optical ranging system," *Applied Optics*, vol. 20, No. 14, 1981, pp. 2389–2394.

Salathe, R.P. et al. "Coupled–mode propagation in multicore fibers characterized by optical low–coherence reflectometry," *Optics Letters*, vol. 21, No. 13, 1996, pp. 1006–1008.

Tearney et al. "Scanning single–mode fiber optic catheter–endoscope for optical coherence tomography," *Optics Letters*, vol. 21, No. 7, 1996, pp. 543–545.

Thurston et al. Analysis of Picosecond Pulse Shape Synthesis by Spectral Masking in a Granting Pulse Compressor, *IEEE Journal of Quantum Electronics*, vol QE–22, No. 5, 1986, pp. 682–695.

Wang et al. "Characterization of fluid flow velocity by optical Doppler tomography," *Optic Letters*, vol. 20, No. 11, pp. 1337–1339.

Webb, Robert H. "Optics for laser rasters," *Applied Optics*, vol. 23, No. 1984, pp. 3680–3683.

Weiner, A.M. et al. "Programmable femtosecond pulse shaping by use of a multielement liquid–crystal phase modulator," *Optics Letters*, vol. 15, No. 6, 1990, pp. 326–328.

Yasa, Zafer A. et al. "A Rapid–Scanning Autocorrelation Scheme for Continuous Monitoring of Picosecond Laser Pulses," *Optics Communication*, vol. 36, No. 5, pp. 406–408.

He, Zuyuan et al. "Selective Image Extraction by Synthesis of the Coherence Function Using Two–Dimensional Optical Lock–in Amplifier with Microchannel Spatial Light Modulator," *IEEE Photonics Technology Letters*, vol. 9., No. 4, Apr. 1997, pp. 514–516.

Tearney, G.J., et al. "High=Speed Phase–and Group–Delay Scanning with a Granting–Based Phase Control Delay Line," *Optical Letters*, vol. 22, No. 23, Dec. 1, 1997, pp. 1811–1813.

Plyaket, Ram, et al. "Programmable Ultrashort Optical Pulse Delay Using An Acousto–Optic Deflector," *Applied Optics*, vol. 34, No. 8, Mar. 10, 1995, pp1445–1453.

Weiner, A.M., et al. "High–Resolution Femtosecond Pulse Shaping," *J. Opt. Soc. Am. B.*, vol. 5, No. 8, Aug. 1988, pp. 1553–1572.

Kinsel et al., "Design and Calibration of an Electrostatic Energy Analyzer—Time–of–Flight Mass Spectormeter for Measurement of Laser–Desorbed Ion Kinetic Engergies," *Journal American Society for Mass Spectrometry*, vol. 6, pp. 619–262 (1995).

Fork, et al. "Real–Time Intensity Autocorrelation Interferometer." *Applied Optics*, vol. 17, No. 22, Nov. 15, 1978, pp. 3534–3535.

* cited by examiner

GRATING BASED PHASE CONTROL OPTICAL DELAY LINE

CROSS REFERENCE TO RELATED APPLICATIONS

This application claims priority under 35 U.S.C. § 120 as a divisional application of U.S. patent application Ser. No. 09/079,687, filed May 15, 1998 now U.S. Pat. No. 6,111,645, which claims priority to Provisional Application Ser. No. 60/046,739, filed May 16, 1997, and also claims priority as a continuation-in-part application to copending U.S. patent application Ser. No. 08/607,787, filed Feb. 27, 1996, which is a continuation-in-part application of U.S. patent application Ser. No. 08/577,366, filed Dec. 22, 1995, now U.S. Pat. No. 5,748,598, and is a continuation-in-part application of U.S. patent application Ser. No. 08/252,940, filed Jun. 2, 1994, now abandoned, and is also a continuation-in-part application of U.S. patent application Ser. No. 08/916,759, filed Aug. 19, 1997, now issued as U.S. Pat. No. 5,784,352, which is an continuation application of U.S. patent application Ser. No. 08/492,738, filed Jun. 21, 1997, now abandoned, which is a continuation-in-part of U.S. patent application Ser. No. 08/033,194, filed Mar. 16, 1993, now U.S. Pat. No. 5,459,570, which is a continuation of U.S. patent application Ser. No. 07/692,877, filed Apr. 29, 1991, now abandoned.

GOVERNMENT SUPPORT

This invention was made with government support under Contract. No. NIH-RO1-EY11289-10 awarded by the National Institutes of Health, Contract No. N00014-94-1-0717 awarded by the U.S. Office of Naval Research, and Contract No. F49620-95-1-0221 awarded by the U.S. Air Force Office of Scientific Research. The government has certain rights in the invention.

FIELD OF THE INVENTION

The invention relates to the field of optical measurement using a rapid scanning optical delay line and more specifically to the field of optical coherence tomography.

BACKGROUND

For many applications in optical ranging and optical imaging using interferometrio based techniques, it is necessary to use a scanning optical delay line as a component of the measurement apparatus. A conventional scanning optical delay line produces a delay by propagating the optical beam through a variable path length. Such a conventional delay line produces a change in phase delay and group delay which is determined by the geometric path length divided, respectively, by the phase velocity and group velocity of light in the medium of propagation.

Previous optical delay scanning devices have largely relied on scanning of the optical path length in order to achieve delay scanning. Devices using linear actuators, spinning mirrors or cam-driven linear slides have been demonstrated. Most current mechanical scanning optical delay lines are not rapid enough to allow in vivo imaging owing to the presence of motion artifacts. Piezoelectric optical fiber stretchers that allow rapid scanning have been demonstrated but they suffer from high power requirements, nonlinear fringe modulation due to hysteresis and drift, uncompensated dispersion mismatches, and poor mechanical and temperature stability. In addition the concept of using a system of diffraction gratings and lenses has been demonstrated for stretching and compressing short optical pulses, pulse shaping and phase control. A combination grating and lens device has been demonstrated for scanning delay in a short pulse autocorrelator. The device produces a change in group delay by angular adjustment of a mirror, however, it does not permit the phase delay to be adjusted independently of the group delay.

Such delay lines are useful in performing Optical Coherence Tomography (OCT). OCT is a relatively new optical imaging technique that uses low coherence interferometry to perform high resolution ranging and cross sectional imaging by illuminating the object to be imaged with low coherence light and measuring the back reflected or back scattered light as a function of time delay or range. Optical ranging and imaging in tissue is frequently performed using a modified Michelson or other type interferometer. Precision measurement of optical range is possible since interference is only observed when the optical path length to the scattering features within the specimen and the reference path optical path length match to within the coherence length of the light.

The axial reflectance of structures within the specimen is typically obtained by varying the reference arm length using a mechanical scanning linear galvanometer translator and digitizing the magnitude of the demodulated interference envelope or direct digitization of the fringes. A cross-sectional image is produced by recording axial reflectance profiles while the position of the optical beam on the sample to be imaged is scanned. Such imaging can be performed through various optical delivery systems such as a microscope, hand-held probe, catheter, endoscope, or laparoscope.

SUMMARY OF THE INVENTION

Unlike conventional scanning optical delay lines, the change in phase delay using a grating based phase controlled delay line is more independently adjustable from the change in group delay, so that when the delay line is used in conjunction with an interferometer, the modulation of interference fringes produced by delay line scanning may be more precisely controlled. In one embodiment a diffraction grating disperses an optical beam into different spectral frequency or wavelength components which are collimated by a lens. A mirror is placed one focal length away from the lens and the alteration of the grating groove density, the grating input angle, the grating output angle, or the mirror tilt produces a change in optical group and phase delay. Specifically, if the mirror tilt produces a change in group delay, the offset of the beam with respect to the center axis of tilt controls the phase delay and the resultant modulation frequency at the interferometer. Moreover, if the grating-lens pair is incident on the center axis of the tilting mirror, group delay is produced without changing the phase delay. Then other external modulation techniques may be applied to control the frequency of modulation of the interference fringes, or OCT detection can be performed directly at baseband using a phase diversity homodyne detection technique.

In the preferred embodiment, the device permits optical delays to be scanned by scanning an angle of a mirror, thus providing higher speed optical delay scanning than conventional optical delay lines which typically require longitudinal or range scanning of mirrors or other optical retroreflecting elements. In other embodiments, the device permits high speed scanning by varying the periodicity of an acousto-optically generated diffraction grating or other device parameters. In addition, since interferometric optical ranging and imaging techniques depend upon the frequency of modulation of the interference fringes produced by the interferometer, this device permits the design of higher performance interferometric ranging and imaging systems.

The optical delay line apparatus is designed so that it may be used with Low Coherence Interferometry (LCI), Optical Coherence Tomography (OCT), or other interferometric based optical ranging and imaging techniques. This apparatus is especially useful for the implementation of OCT in applications which require high speed imaging because these applications require high speed scanning of optical delay. In medical imaging or in vivo imaging applications, the apparatus permits high speed imaging by reducing or eliminating blurring from motion artifacts and permitting real time visualization. The medical applications of this device in OCT imaging include but are not limited to in vivo medical diagnostic imaging of the vascular system; gastrointestinal tract; urinary tract; respiratory tract; nervous system; embryonic tissue; OB/GYN tissue; and any other internal human organ systems. Other medical applications include a rapid scanning OCT system for performing guiding surgical intervention. This device may be also used in OCT imaging for non-medical applications including imaging in biological specimens, materials, composite materials, semiconductors, semiconductor devices and packages, and other applications requiring high speed imaging.

The optical delay lines of the invention presented here are an improvement over existing mechanical delay lines because the sweep speed of the scan can be increased and the phase delay and group delay of the scanning can be more independently controlled. This decoupling of group delay and phase delay permits the control of fringe modulation in a manner not previously possible by other optical delay scanning methods. Additionally, the disclosed delay scheme can be embodied with no moving parts. Finally, this optical delay line apparatus can be incorporated into OCT systems to enable high speed reference arm optical path length scanning using heterodyne or homodyne detection. This scanning technology is necessary for high speed OCT imaging to for a variety of applications (e.g., in vivo medical imaging in human tissue). It has been shown that OCT has ten times greater resolution than intravascular ultrasound (IVUS) and endoscopic ultrasound (EUS) in the application of diagnosing tissue pathology. Similar findings have shown that OCT may be clinically useful for performing high resolution imaging of other organ systems, including the skin and gastrointestinal tract.

The delay line includes common optical components, has modest power requirements, generates repeatable and controllable optical delays, and is temperature stable. Moreover, since the phase delay and group delay are adjustable, the modulation frequency which is produced in interferometric imaging techniques can be controlled thus simplifying the detection electronics. This is especially important for detection scenarios which involve direct electronic digitization (A/D conversion) of the detected optical interference signal.

The grating based phase control optical delay line produces optical group and phase delay by dispersing the spectrum with a grating, and applying a temporally modulated linear wavelength dependent phase. The linear wavelength dependent phase can be achieved by reflecting the spread spectrum from a tilted mirror. If the angle of the mirror is rapidly scanned, a time dependent optical group delay line is produced. The optical delay line can then be inserted into the reference arm of an interferometer for performing high speed OCT.

The phase control delay line is powerful because it allows group delay to be produced by scanning the angle of a beam, instead of employing mechanical linear translation to vary optical path length. The phase control delay line also allows flexibility in the heterodyne or IF beat frequency. Commercially available mechanical beam scanners such as the galvanometer, resonant scanner, rotating polygon mirror, and scanning holographic optical elements are one to two orders of magnitude faster than mechanical linear translators. In addition, rapid optical beam scanning can be performed by devices such as acousto-optic modulators which contain no moving parts. These components are used in a variety of applications such as bar code readers, laser printers, and real time video scanning subsystems.

BRIEF DESCRIPTION OF THE DRAWINGS

This invention is pointed out with particularity in the appended claims. The above and further advantages of this invention may be better understood by referring to the following description taken in conjunction with the accompanying drawings, in which:

DETAILED DESCRIPTION

Figure 1A:
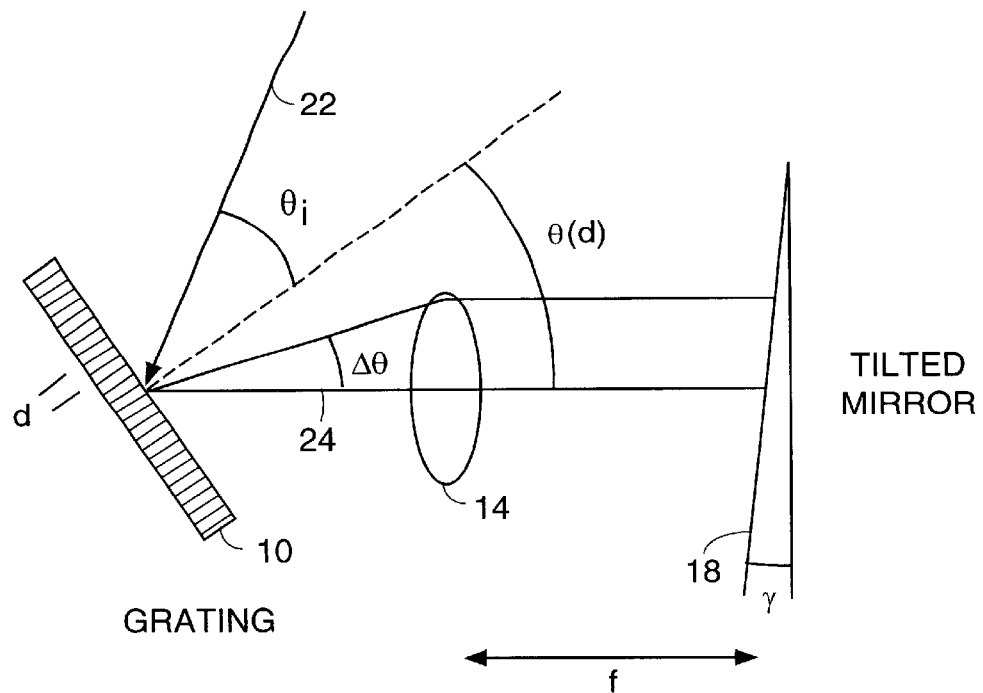
FIGS. 1A and 1B are block diagrams of a grating based phase control optical delay line in a single pass configuration and a double pass configuration, respectively.
Figure 1B:
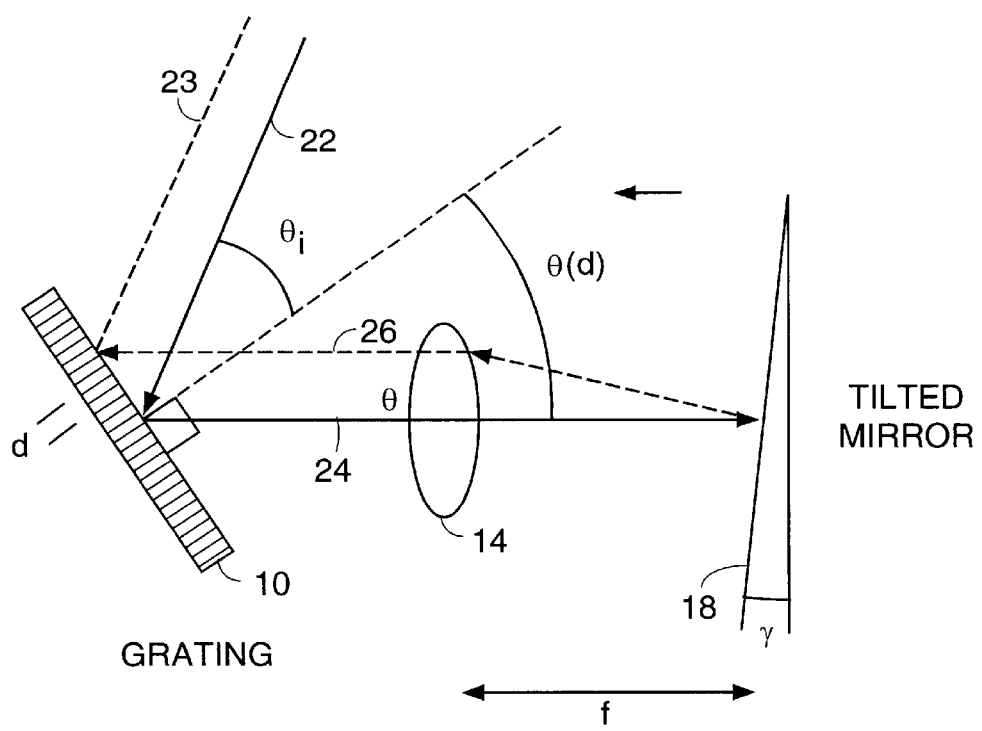

The optical group delay scanning can be accomplished by scanning the components or parameters of the system in a variety of ways. In one embodiment (FIG. 1A), the grating based phase control optical delay line includes a diffraction grating 10 having a grating spacing (d) and lens 14. A mirror 18 is placed approximately one focal length (f) away from the lens 14. The grating 10 disperses the spectrum of the incident optical beam 22. The Fourier transform of the dispersed optical beam 24 is present at the mirror 18. If the mirror 18 is tilted (angle γ), a phase ramp or linear phase shift of the optical spectrum across the mirror 18 is applied. The inverse Fourier transformation of the spectrum is achieved as the light propagates back through the lens 14 toward the grating 10. The inverse Fourier transform of a linear phase shift is a time delay, therefore, as the light is reflected back from the mirror 18, it results in a temporal group delay of the incident beam 22. Changes in group delay can also be made to occur by changing the grating groove density (d), the grating input angle ($\theta_i$), the grating output angle ($\theta$(d)) or mirror tilt (γ). A double passed configuration (i.e., the reflected light 23 approximately follows, in reverse direction, the incident light path 22) as shown in FIG. 1b can be used to assure that the incident optical path 22 is coaxial with the reflected optical path 23. The double passed configuration thus improves coupling of the reflected beam 23 back into the optics used to launch the incident beam 22.

Figure 12:
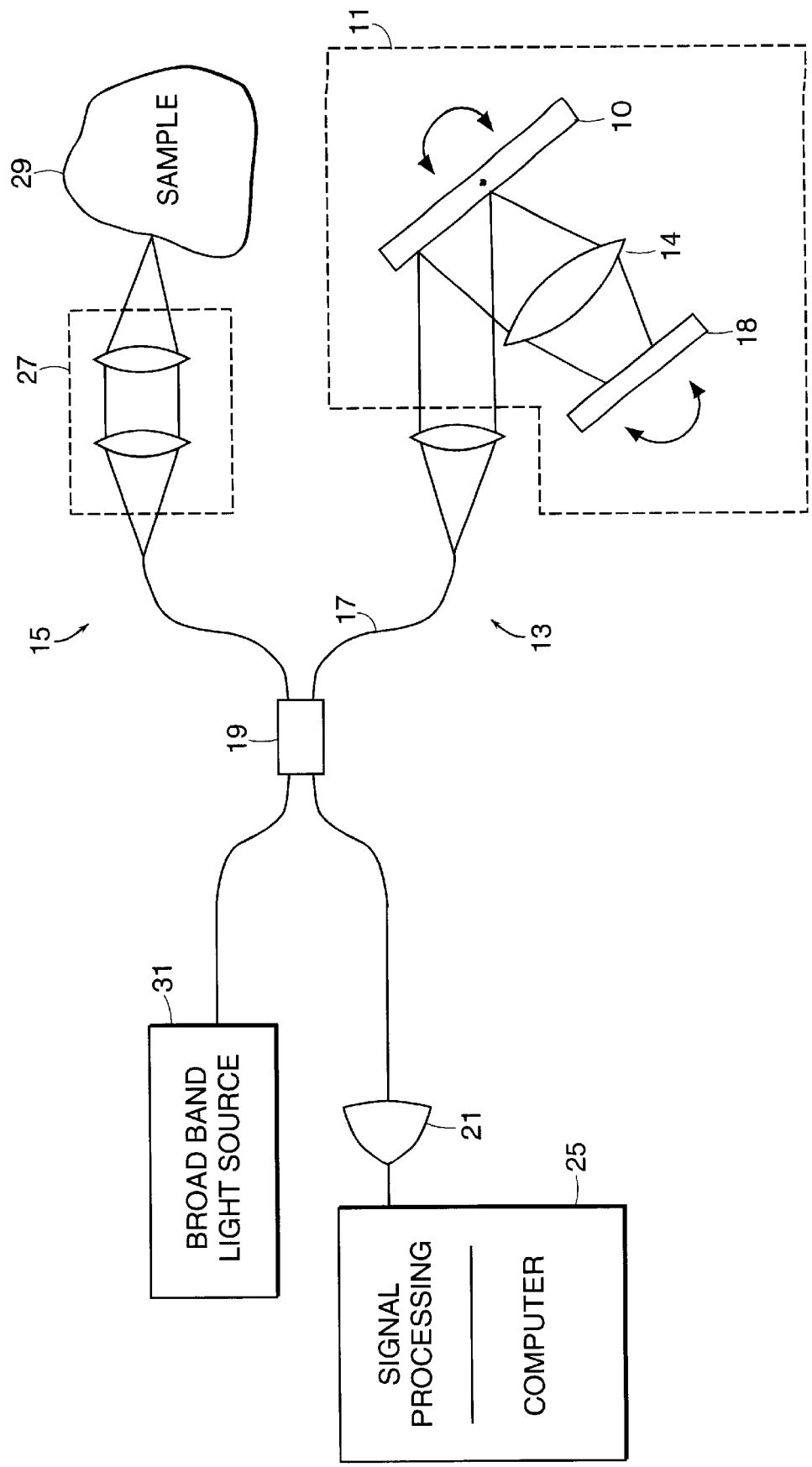
FIG. 12 is a block diagram of a grating based phase control optical delay line in an OCT system.

Referring to FIG. 12, an OCT system using a scanning optical delay line 11 includes an interferometer with a reference path 13, a sample path 15, a splitter/combiner 19, a broadband source 31, a detector 21, and a processor 25. The scanning optical delay line 11 is located at the end of the reference arm 13 of the interferometer. The sample arm 15 includes a probe module 27 to direct light to the sample 29 and collect light scattered from the sample 29.

Figure 2:
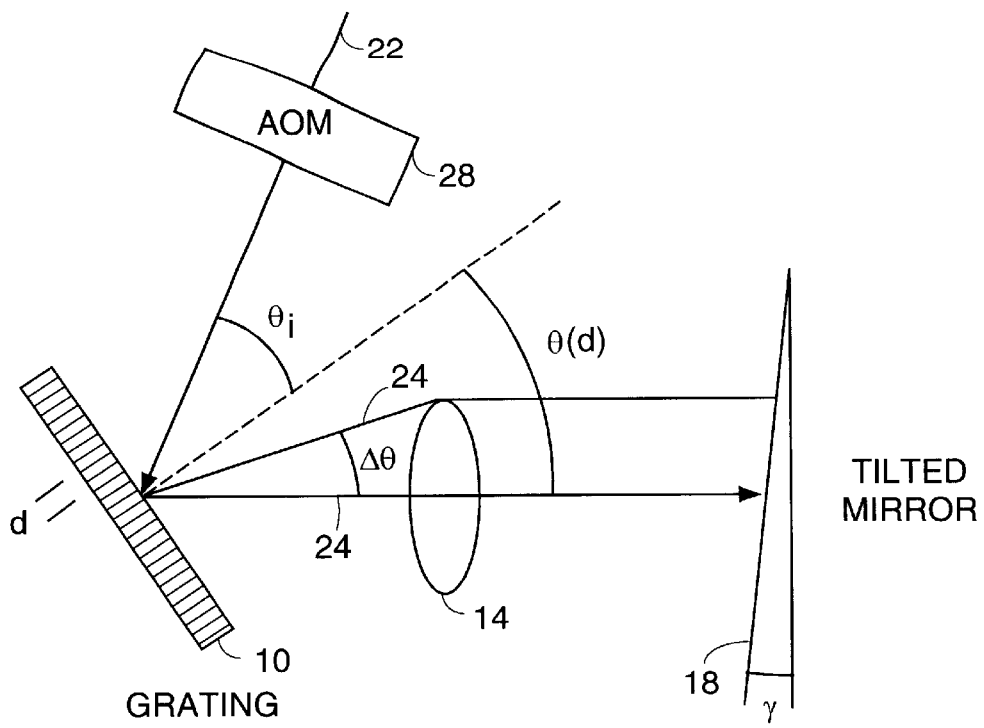
FIG. 2 is a block diagram of a grating based phase control optical delay line using an acousto-optic modulator and a reflection grating to scan an input beam.
Figure 3:
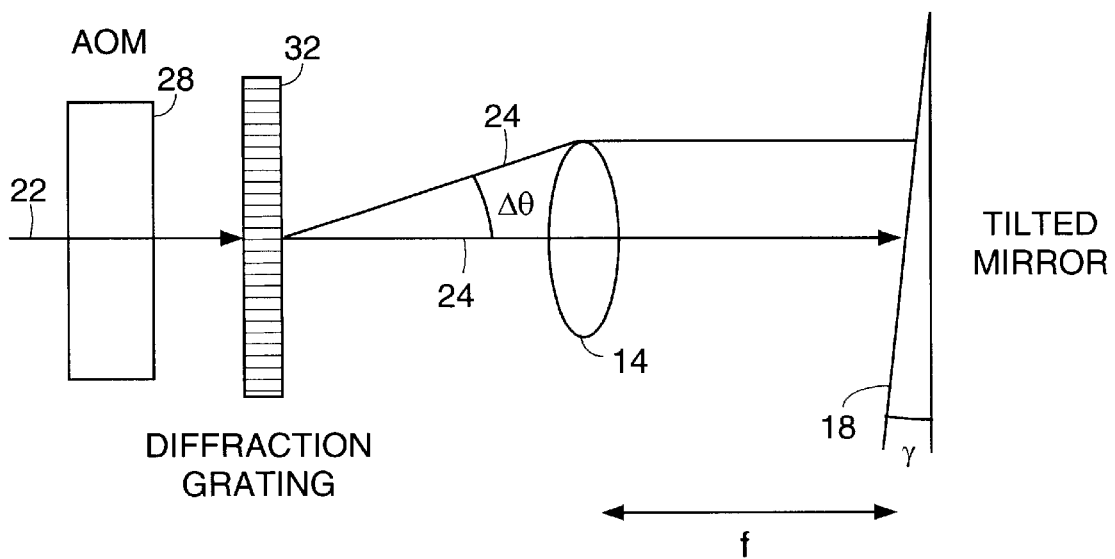
FIG. 3 is a block diagram of a grating based phase control optical delay line using an acousto-optic modulator and a diffraction grating to scan an input beam.

In some embodiments, the grating groove density (d) and grating input angle ($\theta_i$) are varied using an acousto-optic modulator 28 (AOM) (FIGS. 2 and 3). An AOM 28 can scan a beam without using any moving parts. The AOM 28 forms a high frequency sound wave in a crystal which interacts with the crystal to form a variable refractive index grating. Acoustic energy is transferred to the crystal by means of a small piezoelectric transducer (PZT) or other transducer attached to one end. A radio frequency (RF) signal is applied to the PZT to create an acoustic wave in the crystal. This acoustic wave varies the refractive index of the crystal to produce a Bragg grating. The light diffracted by the grating is transmitted through the crystal at an angle determined by the grating spacing. If the RF frequency is scanned, the grating spacing changes, altering the angle. In FIG. 2, the AOM scans the incident angle $\theta_i$. In FIG. 3, the AOM dispersion of the incident beam 22 is augmented by directing the light transmitted through the AOM 28 through a diffraction grating 32. The second grating 10,32 is used to increase the dispersion produced by the AOM 28 and increase the group delay. In another embodiment, a telescope is used in between the AOM 28 and the grating 10 as shown in FIG. 2.

A configuration using an AOM 28 has the additional advantage of no moving parts in the rapid scanning optical delay line. In addition, this configuration can achieve higher scanning speeds than many existing methods. Moreover, changes in coupling and phase fringe modulation frequency can be compensated for by applying a customized AOM RF input signal. For example, if the amplitude of the diffracted light decreases with the AOM scan angle then the PF drive amplitude can be increased to compensate. More importantly, if the output angle is not linear with RF drive frequency, then the RF drive waveform can be adjusted from a single sawtooth or triangle waveform to compensate for a linear output angle or other desirable output angle (e.g., a sinusoidal output angle) as a function of time.

In yet another embodiment (FIG. 4) the mechanical optical delay scanning apparatus functions by changing the grating input angle ($\theta_i$), using a polygon scanning mirror 34, a galvanometer, resonant scanner, or a piezoelectric mirror tilter in the path of the incident beam 22. A telescope 36 is placed between the scanning mirror 34 and the grating 10 to avoid beam walkoff at the grating 10. If γ is non-zero, the delay is scanned as the angle of the mirror 34 is scanned.

Figure 5:
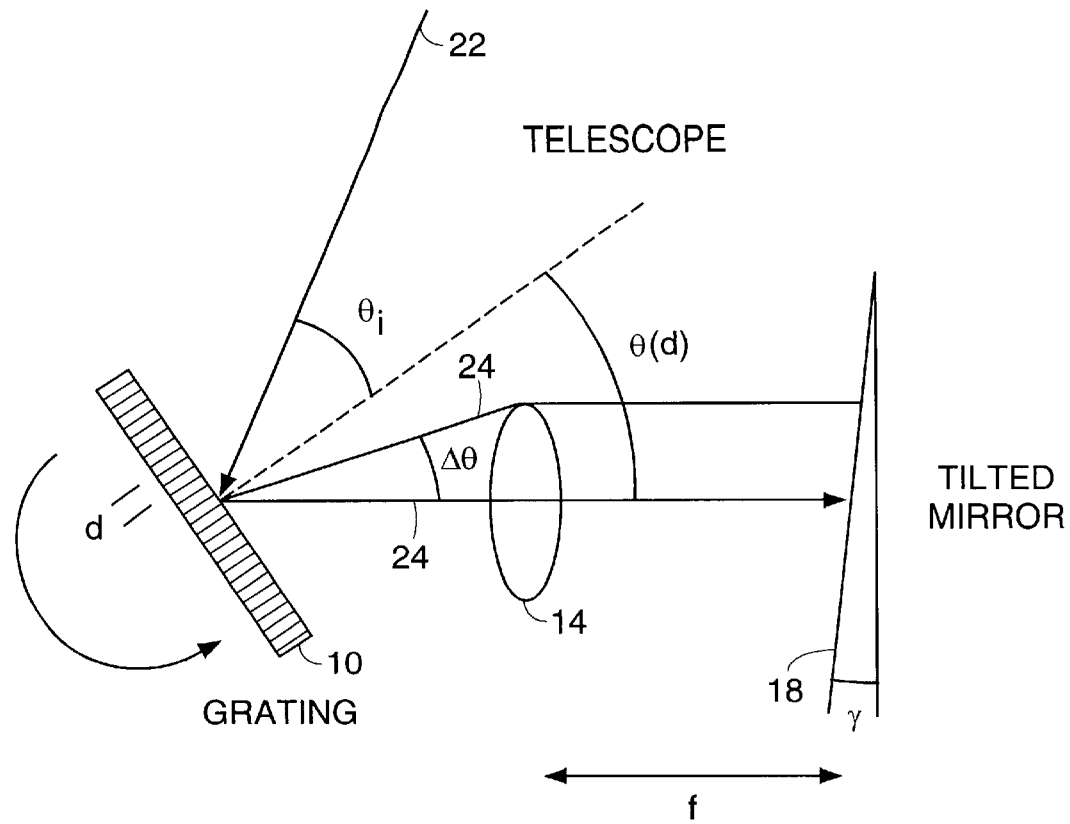
FIG. 5 is a block diagram of a grating based phase control optical delay line using a steerable grating.

In still another embodiment (FIG. 5), the grating 10 can also be physically or mechanically scanned in angle using a galvanometer, a resonant scanner, or a piezoelectric mirror tilter. For example, a small light weight grating can be placed on the rotating shaft of a galvanometer to achieve a steerable grating 10.

Figure 4:
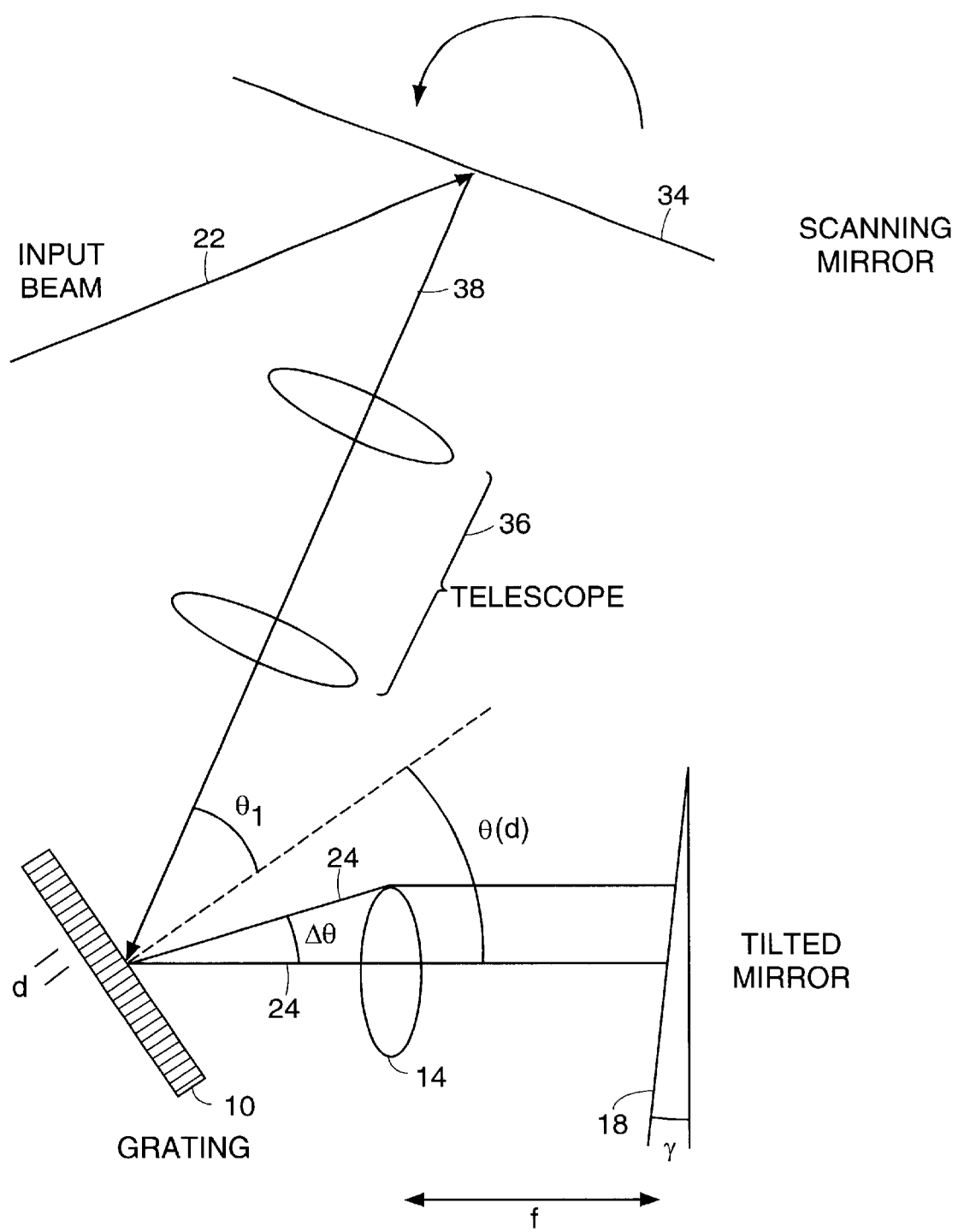
FIG. 4 is a block diagram of a grating based phase control optical delay line using a scanning mirror to change the grating input angle.
Figure 6:
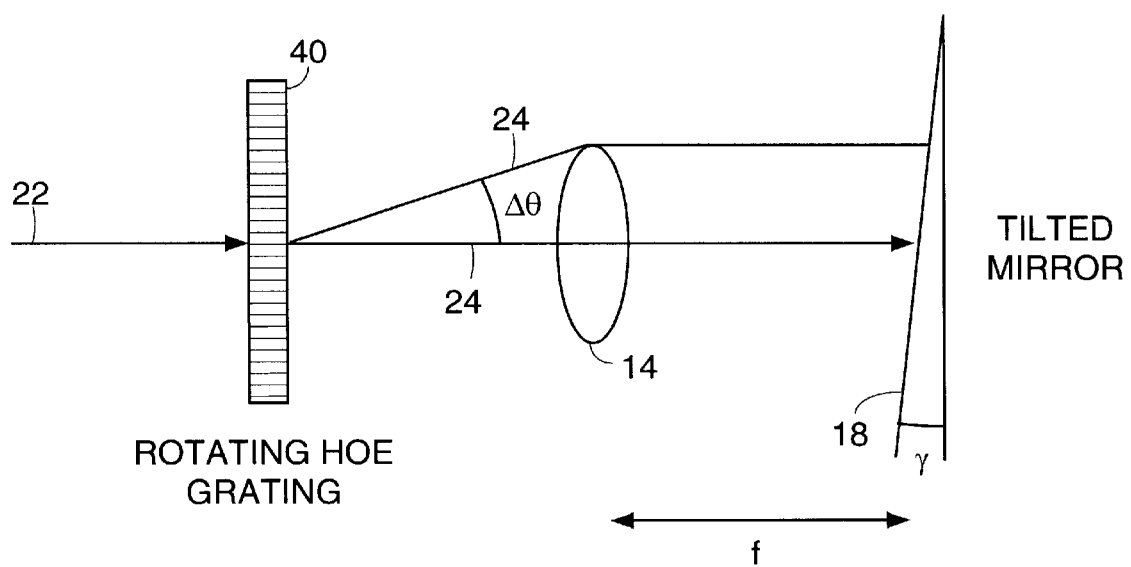
FIG. 6 is a block diagram of a grating based phase control optical delay line using a radially scanned circular holographic optical element.
Figure 9A:
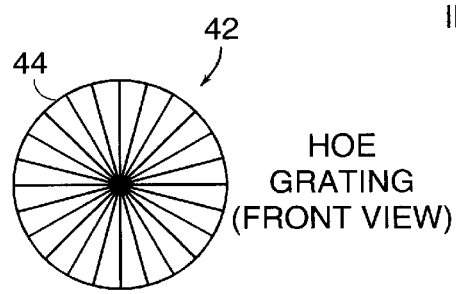
FIGS. 9A and 9B show a circular holographic optical element which can be used as a diffraction grating in a grating based phase control optical delay line.
Figure 9B:
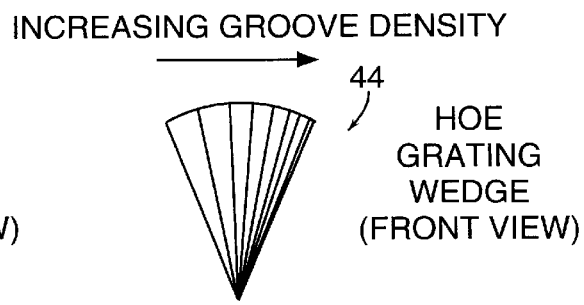

In an embodiment in which the grating 10 is a circular holographic optical element 40 (HOE), the grating 40 may be radially scanned (FIG. 6). The HOE 40 changes the transmitted diffraction angle (Δθ) of a beam as it is rotated. One simple configuration consists of a circular element 42 with wedge subsections 44 (FIG. 9a). Each wedge consists of a diffraction grating with grating spacing (d) that varies as a function of angle (θ) (FIG. 9b). As the HOE 42 is rotated, d and Δθ(λ) change, producing a varying group delay. If the HOE 42 is rotated using a high speed motor, the change in grating spacing d diffracts the beam at a different angle θ. Usually the holographic scanner 42 is only used with monochromatic light. The grating 10 can spatially disperse a broad bandwidth source. This property is advantageous for phase control because the rotating HOE grating 42 can replace both the grating 10 and the angular scanner 18,34 (FIGS. 1 and 4, respectively).

Figure 7:
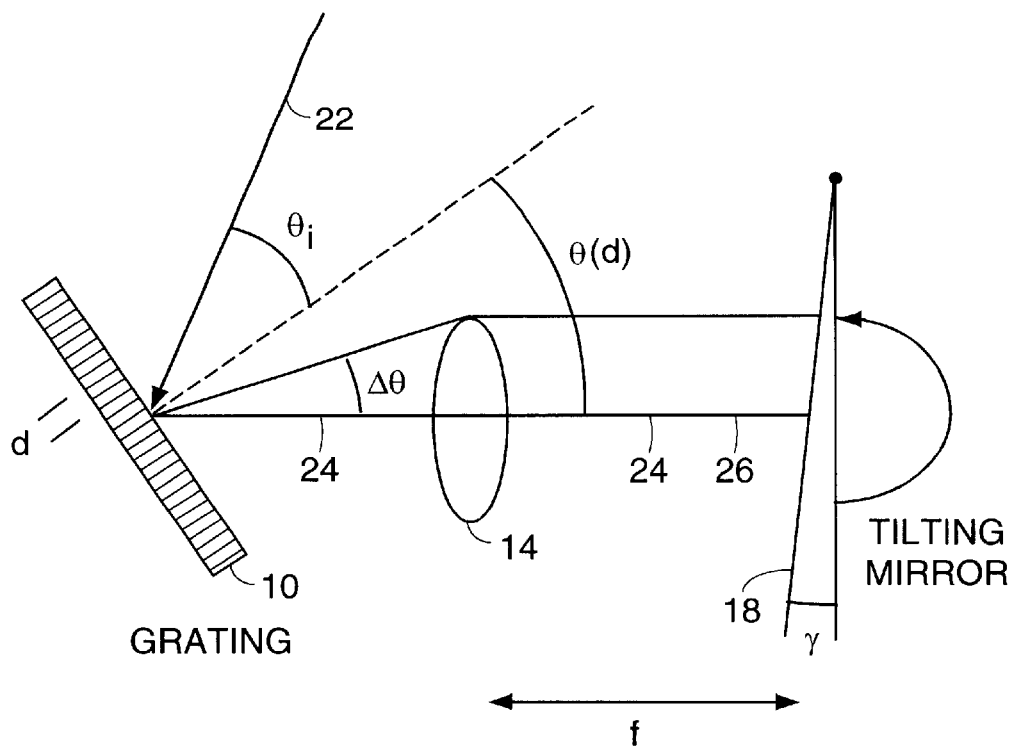
FIG. 7 is a block diagram of a grating based phase control optical delay line having a scanning mirror.

In still yet another embodiment (FIG. 7), in either a single pass or a double pass configuration, the angle (γ) of the mirror 18 following the grating 10 and lens 14 can be scanned using a polygon scanning mirror, a galvanometer, resonant scanner, or a piezoelectric mirror tilter.

Figure 8:
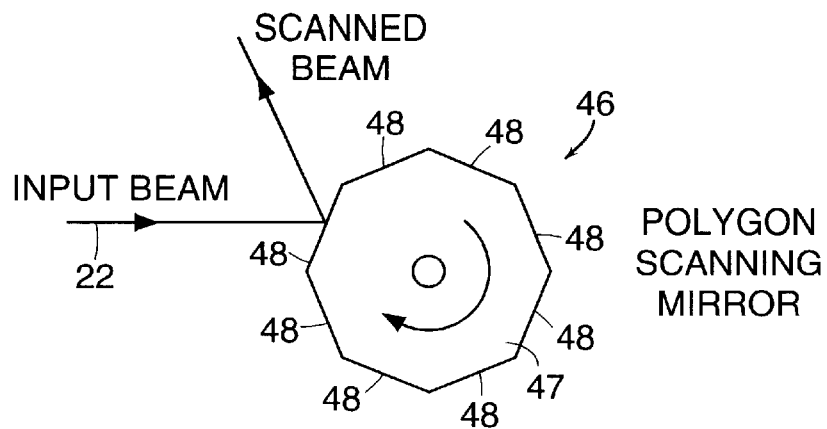
FIG. 8 is a block diagram of a machined polygon with reflecting facets which can be used as a scanning mirror.

A polygonal scanning mirror 46 (FIG. 8) consists of a machined polygon 47 with highly reflecting facets 48. A high speed motor (not shown) is used to rotate the polygon 47. As the polygon 47 rotates, the input beam 22 is reflected off of one of the facets 48, producing an angular scan. Since air bearing motors are available that can scan at up to 40,000 rpm, a polygonal scanning mirror 46 with 24 facets 48 can produce 16,000 angular scans per second. This technology is well-suited for generating linear angular scans at high speeds.

A galvanometer used for linear mechanical scanning of optical delay includes a retroreflector or corner cube mounted on a lever arm. Due to mechanical resonances and the large force required to drive the relatively high moment of inertia associated with a retroreflector mounted to a lever arm, the maximum frequency of galvanometer-based linear translators is typically only approximately 100 Hz. The galvanometer is similar in structure to a torque motor, consisting of a mirror mounted to a moving magnet rotor positioned between stator coils. The stator coils can provide a variable magnetic field which causes the rotor to turn. Without the large mass of a lever arm, this device is capable of angular scanning with high linearity and frequencies up to a few kHz. Scanning frequencies are maximized by reducing the mass of the rotor and attached mirror. Thus, for high scan frequencies, the mirror must be small in size, limiting the maximum beam size on the mirror. A linear angular scan is possible because the galvanometer is heavily damped to prevent coupling into its natural mechanical resonances.

A resonant scanner can also be used. The resonant scanner only oscillates at or near its mechanical resonance frequency. Thus, resonant scanners produce a sinusoidal change in angle as a function of time. If the near linear portions of the rising and falling edges of the sinusoidal angular scan are used, a 66% duty cycle can be achieved with a 2:1 slope change. Thus, for applications which require a linear angular scan (e.g., OCT imaging in which the interference output of the interferometer is detected and demodulated using a fixed band pass filter), the resonant scanner can provide a 66% duty cycle with a signal-to-noise (SNR) loss that is dependent on the noise equivalent bandwidth (NEB). The resonant scanner, however, can oscillate at speeds up to 20 kHz, permitting its use for real time OCT imaging if the decreased SNR is acceptable. By way of example, if each scan of the optical delay is used to acquire an axial set of image pixels, then images of 500 pixels at 15 to 30 image frames per second correspond to 7.5 to 15 kHz scan frequencies.

Alternatively, a resonant galvanometer can be used with resulting nonlinear phase and group delays as a function of time. This nonlinear behavior can be compensated using post-detection electronic processing as is known in the art (e.g., a Doppler tracking receiver). For many delay line applications such as OCT, it is sometimes desirable to have a non-zero IF frequency or heterodyne frequency that results when the output of the delay line is interferometrically combined with some of the original light not transmitted through the delay line and photodetected. By offsetting the center of rotation of the tilt mirror 18 relative to the chief ray passing through the lens 14, the heterodyne frequency can be adjusted. Since the phase and group delay are decoupled in this process, the heterodyne frequency can be adjusted without affecting the group delay. Moreover, if the grating 10 and lens 14 are located on an axis which intercepts the axis of the tilting mirror 18, group delay is produced without changing the phase delay. This configuration can be used to apply an external modulation to the local oscillator for optimal matching of the optical heterodyne frequency to the system demodulation electronics or for performing homodyne detection in an OCT imaging system.

In addition, a double passed configuration can be used in all of the scanning methods described above to ensure that the incident optical path 22 is coaxial with the reflected optical path. Thus, the double passed configuration eliminates the lateral offset of the reflected beam 23 (shown in FIG. 1) and thus improves the coupling efficiency back into the light path 22. All of the above methods provide a way to change both optical group delay and phase delay, thus allowing control over the optical fringe modulation frequency.

Figure 10:
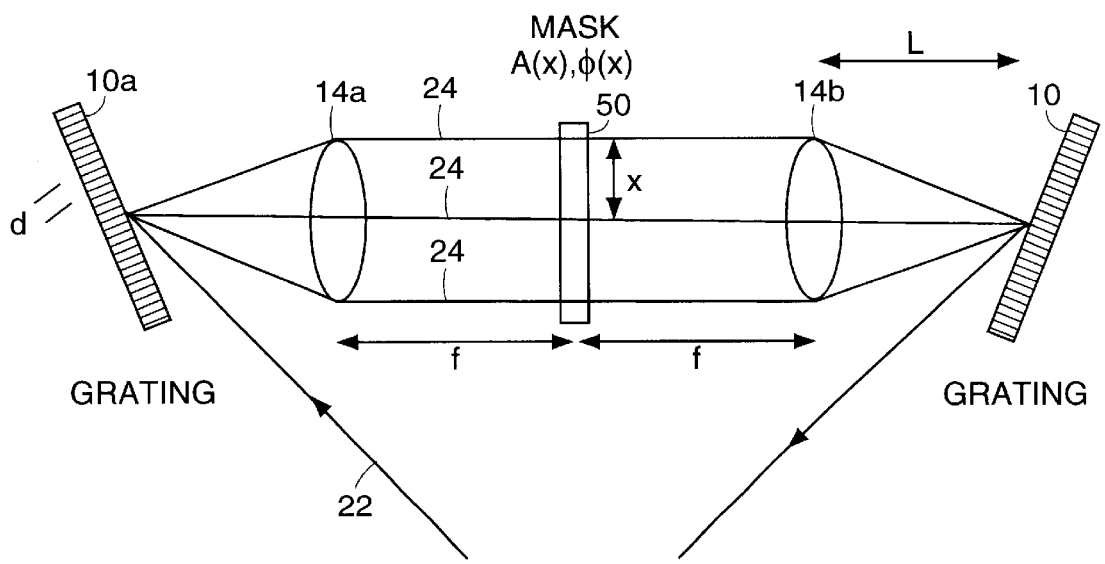
FIG. 10 is a block diagram of a generic pulse shaping apparatus for delay line scanning in OCT systems.

When combined with angular beam scanning, the phase control optical delay can be a versatile method for producing a scanning optical group delay. Phase control is a technique that uses a lens-grating pair 10,14 to alter the temporal properties of ultrafast pulses by manipulating the spectrum. This technique has been used for the temporal shaping of ultrafast pulses. A schematic of the generic pulse shaping apparatus is shown in FIG. 10. The pulse shaping apparatus consists of two identical reflection grating-lens pairs 10,14 and an amplitude, A(x), and/or phase, φ(x) mask 50 placed midway between and one focal length, f, away from both lenses 14. The grating disperses the spectrum of the incident optical beam. If the separation between the lens 14a and grating 10a is equal to the focal length of the lens (i.e., L=f), the Fourier transform of the dispersed optical beam 24 occurs at the mask 50. The mask 50 modifies the spectrum either by phase or amplitude modulation. The modified spectrum is inverse Fourier transformed by the second lens 14b, causing an alteration of the temporal profile of the pulse. This transmission system can be used for delay line scanning in OCT systems.

Figure 11:
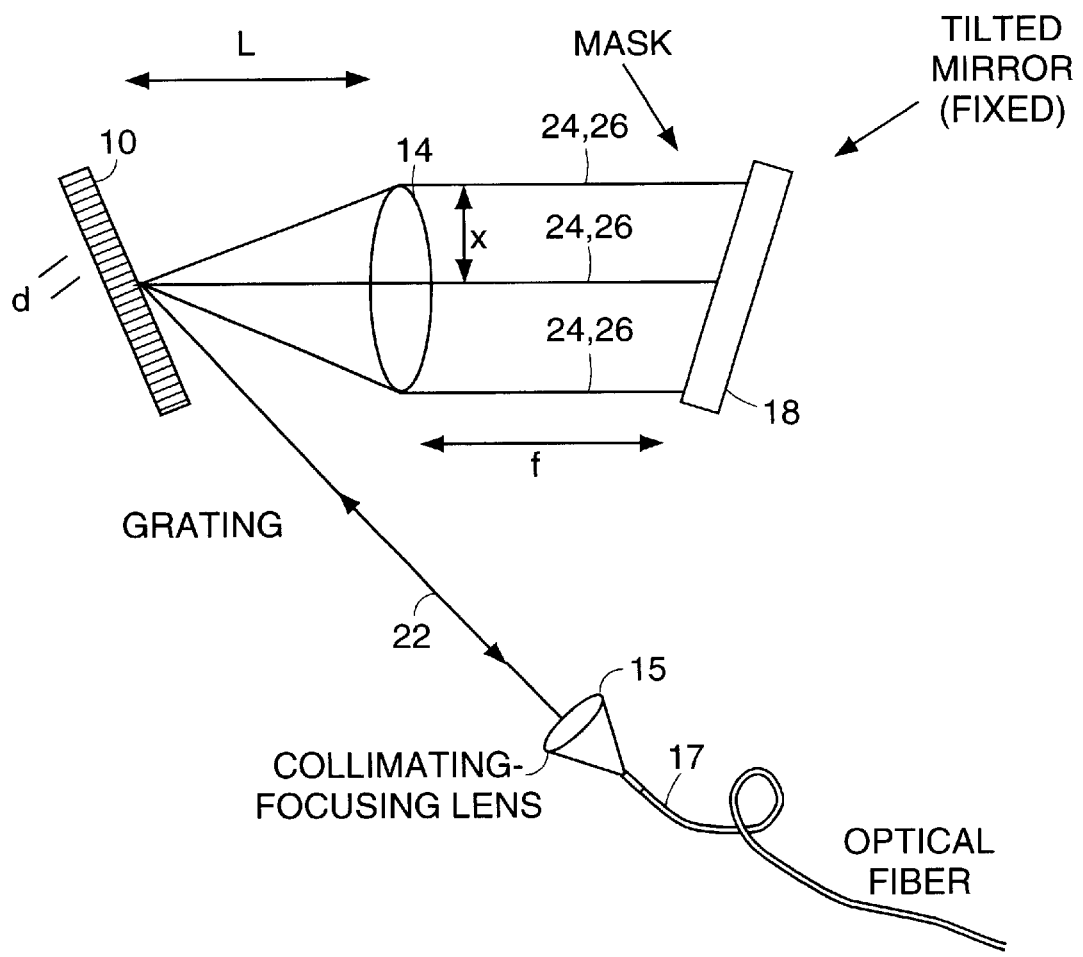
FIG. 11 is a block diagram of a tilted mirror configuration for pulse shaping.

In another embodiment, the pulse shaping apparatus employs a folded geometry configuration (FIG. 11). This configuration has two advantages. First, only one grating-lens pair 10,14 is used. In addition, the folded geometry enables coupling back into the reference arm collimating lens 15 and optical fiber 17 without additional optical components.

Phase manipulation can provide optical group delay by dispersing the spectrum with a grating and then applying a temporally modulated linear wavelength dependent phase. The wavelength dependent angular diffraction of the incident collimated beam is given by the grating equation, $$\theta(\lambda) = \arctan\left(\frac{m\lambda}{d} - \sin(\theta_i)\right), \tag{1}$$

where m is the diffracted order of the reflected beam 24, d is the ruling spacing of the grating 10, and $\theta_i$ is the incident angle on the grating 10. If L=f, each wavelength is distributed along the x axis after the lens, at the position, $$x(\lambda) = f \tan(\theta_0 - \theta(\lambda)) \tag{2}$$

where $\theta_0$ is the diffracted angle the center wavelength of the source, $\lambda_0$. The Fourier transform of the input beam now resides at the plane of the mirror 18. Since the Fourier transform of a linear phase ramp in the spectral domain corresponds to a delay in the time domain, a temporal group delay is obtained by placing a phase mask at the mirror, and is described by:

$$\phi(x(\lambda)) = -x(\lambda)\tau \tag{3}$$

The modified spectrum is then inverse Fourier transformed by propagating back through the folded phase control apparatus, creating a temporal delay of the input beam 22. The magnitude of the optical delay is proportional to the spectral dispersion of the grating 10, the focal length of the lens 14, and the slope of the phase ramp, τ. Note that as described later by offsetting the center of rotation of the mirror 18 (FIG. 1a) with respect to the chief ray at angle $\theta_0$, the phase control device can be used to independently adjust the phase delay and group delay.

Arbitrary phase masks, such as a liquid crystal arrays, have been proposed for pulse shaping, however, a complicated phase mask is not necessary for producing an optical group delay only. Instead, the phase-mask-mirror combination can be replaced with a single tilted mirror (FIG. 11). If the mirror 18 is tilted with an angle (γ), a linear wavelength dependent phase is applied to the incident beam 24. A 100 Hz linear scanning group delay line using a piezoelectric mirror tilter has been previously presented for construction of a high speed autocorrelator to measure pulse durations.

Figure 13:
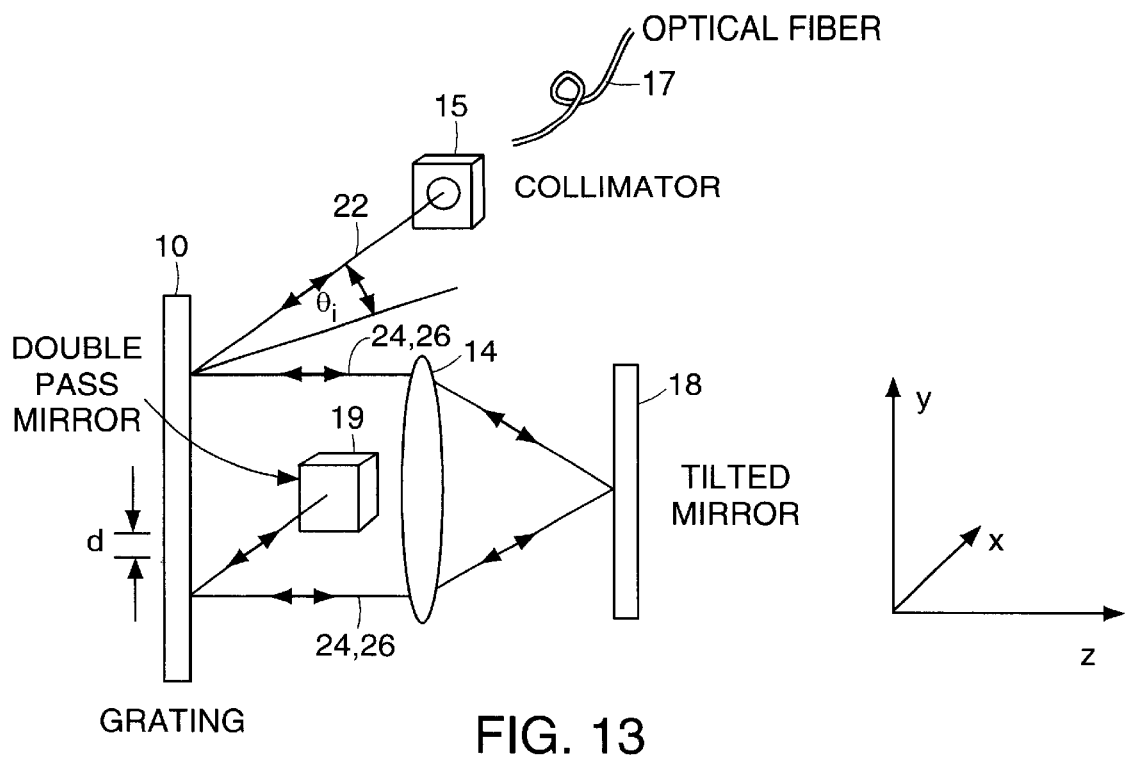
FIG. 13 shows a block diagram of a grating based phase control optical delay line in a double pass configuration.

One difficulty with using a tilted mirror 18 to produce the group delay is that the light 26 reflected from the tilted mirror 18 is no longer collinear with the incident beam 24. Beam walkoff due to deflection by the tilted mirror 18 limits coupling of the reflected beam 26 back into the reference arm collimating lens 15 and single mode fiber 17 (FIG. 12). One solution is to use a double pass configuration (FIG. 13). In this configuration, the beam emerging from the collimating 15 is decentered on grating 10 so the diffracted beam 24 is decentered on the lens 14. The beam 24 is refracted by the lens 14, which is corrected for spherical aberration, onto the tilted mirror 18. The tilted mirror 18 reflects the beam 26 through the lower portion of the lens 14. The light is then diffracted off the grating 10 and onto the double pass mirror 19. The double pass mirror 19 is aligned to allow the beam 26 to retrace its path back to the collimator. This configuration allows the folded configuration to be used with a tilted mirror 18 while avoiding beam walkoff and resultant coupling losses into the optical fiber 17 or equivalent source. In addition, since the phase control apparatus is double passed, the delay produced for a given mirror tilt is also doubled. All of the devices described can use some form of this double pass geometry.

In addition to enabling high speed group delay scanning, another advantage of the phase control apparatus for OCT is the capability to compensate dispersion mismatch between the reference and sample arms. An analysis performed to determine the group velocity dispersion (GVD) for a grating compressor describes the dispersion in the double passed configuration to be, $$\left.\frac{d^2\phi}{d\omega^2}\right|_{\omega_0} = -\frac{\lambda_0^2(L-f)}{\pi c^2 d^2}[\cos(\theta_0)]^{-3/2}. \quad (4)$$

When the lens 14 is not one focal length away from the grating 10, an additional wavelength dependent phase delay is added to the pulse, creating positive dispersion for L<f or negative dispersion for L>f. This property of the phase control apparatus enables compensation of the dispersion imbalance between the reference and sample arms in the OCT system by simply changing the lens-grating separation.

Figure 14:
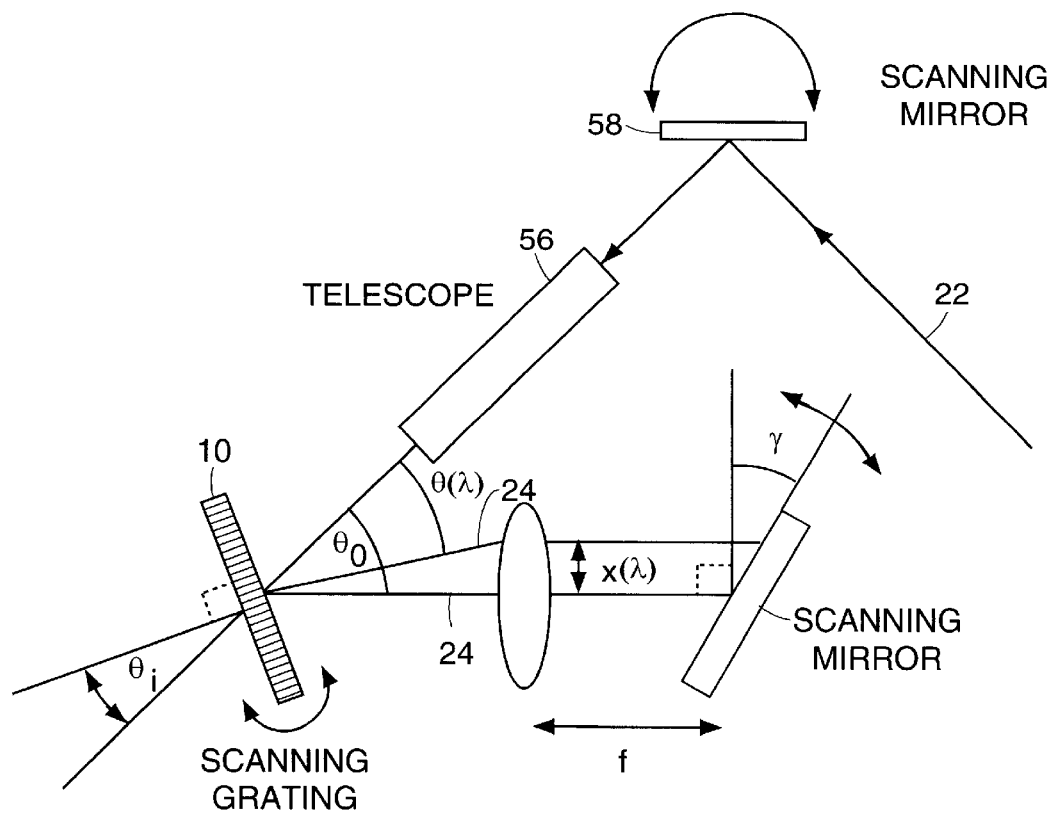
FIG. 14 shows a grating based phase control optical delay line with elements that can be modified to change the scanning group delay.

One powerful aspect of the phase control paradigm is its versatility. Analysis has revealed that altering any one of several optical comments in the phase control apparatus can produce a change in group delay (FIG. 14). Specifically, a scanning group delay can be obtained by tilting the mirror 18, changing the incident angle $\theta_i$ on the grating 10, tilting the grating 10, or changing the grating spacing d.

A simple ray trace analysis can be used to determine an approximate analytical expression for the group delay produced by changing the Fourier plane mirror tilt 10 by an angle, $\gamma$. The wavelength dependent phase shift produced by the tilted mirror 18 can be easily determined from the geometry of FIG. 13 or FIG. 14, $$\phi(\lambda) = -2kz(\lambda) \quad (5)$$

or $$\phi(\lambda) = -2kx(\lambda)\tan(\gamma). \quad (6)$$

The diffracted angle for the center wavelength of the source is $$\theta_0 = \theta(\lambda_0) = \arcsin\left(\frac{\lambda_0}{d} - \sin(\theta_i)\right). \quad (7)$$

If the phase delay is reformulated as a function of frequency, the wavelength dependent phase shift induced by the folded phase control apparatus is, $$\phi(\omega) = -2\frac{\omega}{c}f\tan(\gamma)\tan\left(\theta_0 - \arcsin\left[\frac{2\pi c}{\omega d} - \sin(\theta_i)\right]\right). \quad (8)$$

Since the group delay is defined as $$\tau_g(\gamma) = \left.\frac{\partial\phi}{\partial\omega}\right|_{\omega_0}, \quad (9)$$

after differentiation and substitution of the center wavelength, $$\lambda_0 = \frac{2\pi c}{\omega_0}, \quad (10)$$

the group delay becomes $$\tau_g(\gamma) = -\frac{2f\lambda_0\tan(\gamma)}{cd\cos(\theta_0)}. \quad (11)$$

The change in group delay is twice that of equation (11) for the double passed phase control system. Given the double passed group delay length, $l_g=2\tau_g c$, for small angular deviations of the mirror by $\gamma$, the total group delay length is a linear function of the scan angle, $$l_g(\gamma) = -\frac{4f\lambda_0\gamma}{d\cos(\theta_0)}. \quad (12)$$

For values at Littrow's angle, $$\theta_i = \theta_L = \arcsin\left(\frac{\lambda}{2d}\right), \quad (13)$$

d=150 lines per mm, $\Delta\gamma=10°$, and f=10 cm, the total group delay length calculated using equation (12) is 14 mm.

Since rapid scanning requires a small mirror, vignetting of the spectrum is a potential problem. The beam spread on the mirror 18, $$\Delta x(\lambda_{max},\lambda_{min})=f(\tan[\theta(\lambda_{max})]-\tan[\theta(\lambda_{min})]), \quad (14)$$

determines the maximum allowable mirror size for the rapid scanning delay line. For the parameters given above with a $\lambda_{max}-\lambda_{min}$ bandwidth of 200 nm, the beam spread is 3 mm. Thus, the mirror 18 must be at least 3 mm or clipping of the spectrum will occur, resulting in the convolution of the autocorrelation function with a sinc function. For this reason, other configurations of the phase control apparatus that do not require a moving mirror 18, can be utilized for high resolution applications.

Optical group delay may also be produced by scanning the grating incident beam angle, $\theta_i$, using a scanning component 58 such as a rotating polygon mirror, a galvanometer, or a resonant scanner (FIG. 14). The configuration differs from the previous method by the inclusion of a fixed angle, $\gamma$, a device for scanning $\theta_i$, and a telescope 56 between the scanning mirror 58 and the grating 10. Since the tilted mirror 18 is fixed, it can be large enough to accommodate any bandwidth source. The telescope 56 is inserted between the scanning component 58 and the grating 10 to prevent beam walkoff at the grating 10. To accomplish this, the image and object planes of the telescope 56 must match the positions of the scanning mirror 58 and the grating 10.

Figure 15:
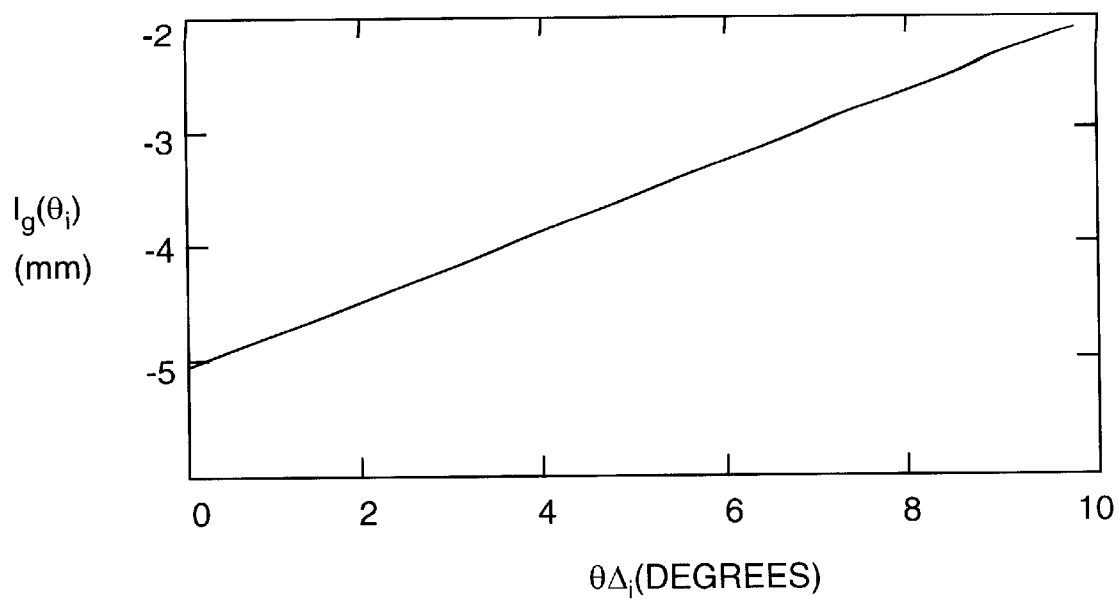
FIG. 15 shows a plot of the path length delay as a function of the grating input angle, $\theta_i$.

An analytical expression for the optical group delay produced by this configuration can be formulated in a similar manner to the scanning mirror configuration, except the independent variable is now $\theta_i$. If $\gamma$ is small, after differentiation of the wavelength dependent phase and evaluation at the center wavelength, the double passed group delay length, $$l_g(\theta_i) = \qquad (15)$$

$$-4f\tan\gamma \left[ \left\{ \theta_{i0} - \left( -\arcsin\left(\frac{\lambda_0}{d} - \sin(\theta_i)\right) \right) \right\} + \frac{\lambda_0}{d\sqrt{1 - \left(\frac{\lambda_0}{d} - \sin(\theta_i)\right)^2}} \right],$$

where $\theta_{i0}$ is the angle of diffraction from the grating 10 for $\lambda_0$ for the central scan position. A plot of the path length delay calculated from equation (15) is shown in FIG. 15 for d=150 lines per mm, f=10 cm, $\gamma=3°$, and a variation of the grating incident angle $\theta_i$ by 10°. For these parameters, the delay obtained using this method is also an approximately linear function of the independent variable, $\theta_i$.

Figure 16:
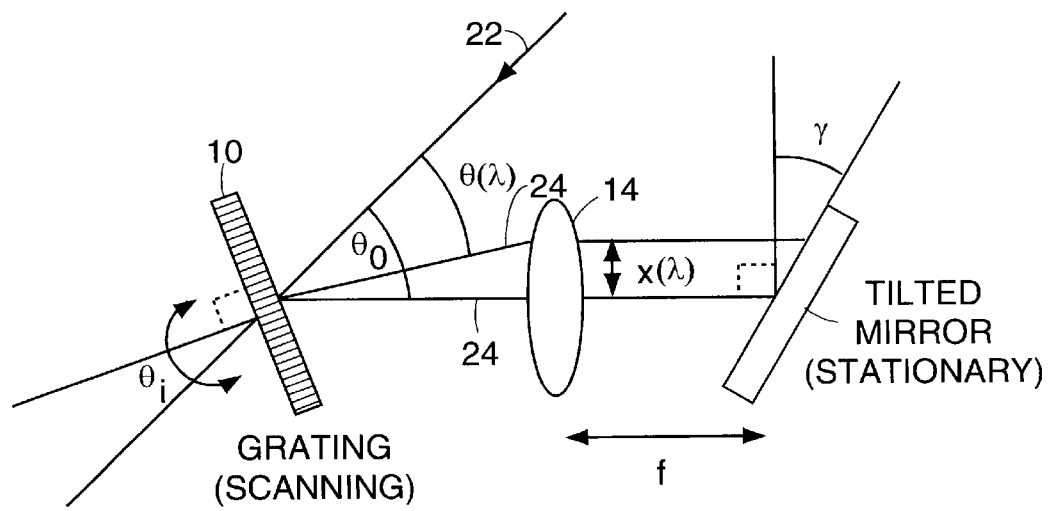
FIG. 16 is a block diagram of a grating based phase control optical delay line using a scanning grating.

Angular scanning of the grating 10 in the folded phase control apparatus also creates a group delay (FIG. 16). The primary advantage to this configuration is that a telescope 56 is not necessary because beam walkoff at the grating 10 does not occur. This approach requires placing a grating 10 on a galvanometer mirror or polygon scanning mirror as shown.

Figure 17:
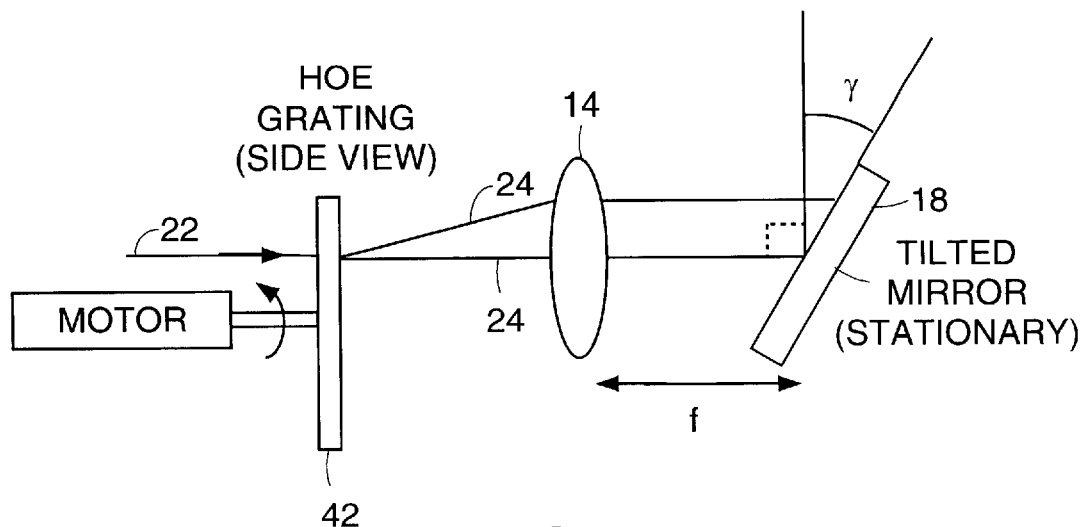
FIG. 17 shows a block diagram of a scanning optical delay line apparatus using a rotating circular holographic optical element to produce a scanning group delay.

Another interesting modification of the phase control apparatus permits high speed group delay scanning. If the grating 10 is a transmission HOE, such as that shown in FIG. 9, the groove density of the grating may be scanned in a rapid fashion. This may be accomplished by using a rotating circular HOE 42 with grating spacing that varies as a function of angle. As the HOE 42 is rotated, the change in grating spacing alters the extent of the spectral spreading (FIG. 17). Since the wavelength dependent phase delay is proportional to ruling of the grating, rotating the HOE 42 also produces a scanning group delay.

Figure 18:
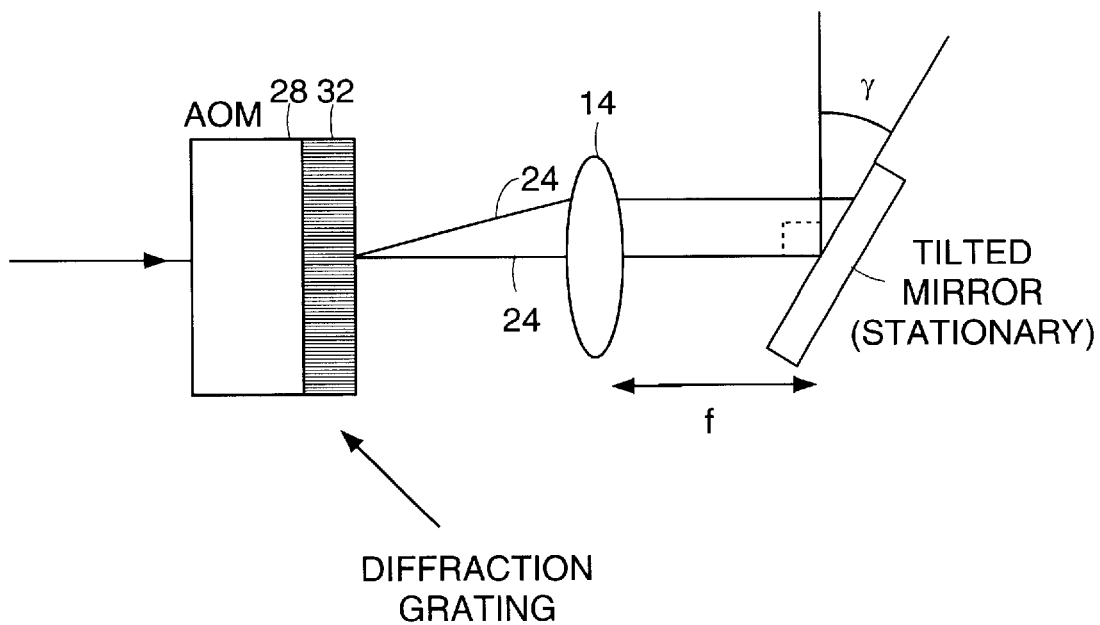
FIG. 18 shows a block diagram of a scanning optical delay line apparatus using an acousto-optic modulator and a diffraction grating.

A more elegant method for changing the grating groove density is the use of an AOM 28 (FIG. 18). In this configuration, the wavelength spread is augmented by directing the light 24 transmitted through the AOM 28 through a diffraction grating 32 (FIG. 18). The diffraction grating 32 is necessary because the change in grating spacing (RF bandwidth) for commercially available AOMs 28 is not sufficient to produce an adequate group delay scan for OCT. A telescope (not shown) with a high magnification can be placed between the AOM 28 and the grating 32 to enhance the change in diffraction provided by the AOM 28.

Figure 19:
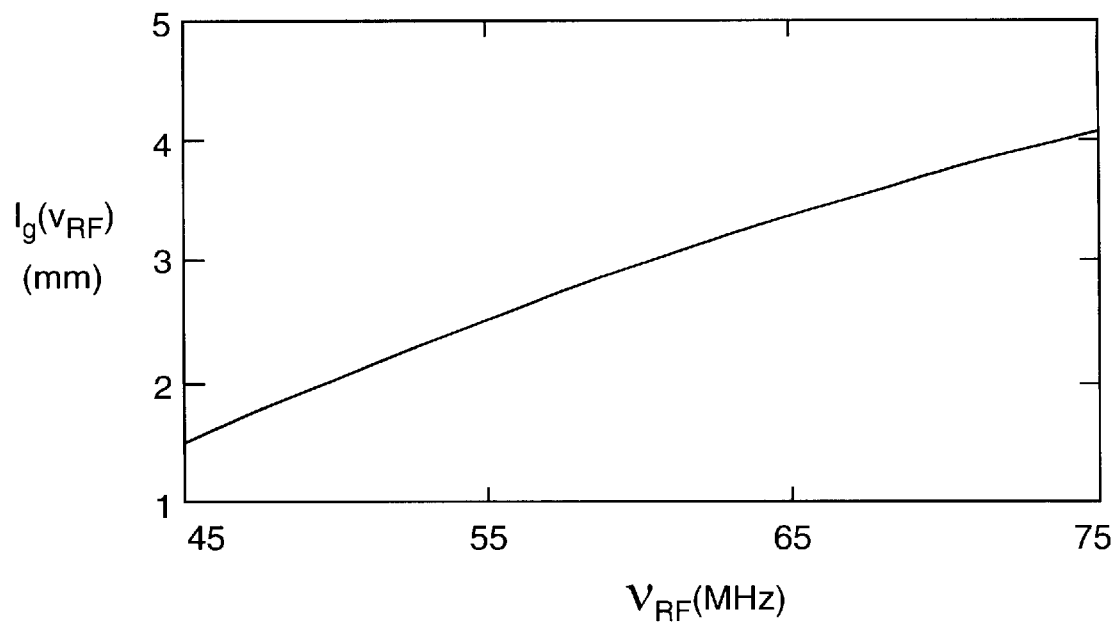
FIG. 19 shows a plot of the path length delay produced by the apparatus of FIG. 18 as a function of the RF driving frequency.

A plot of the path length delay produced by an AOM-diffraction grating pair 28,32 as a function of the RF driving frequency is presented in FIG. 19. To generate this data, an analytical expression of the group delay for a changing grating spacing, d, was formulated. The parameters used for generating the data include the use of a slow shear wave $TeO_2$ AOM 28 ($c_s$=0.6 km/s, n=2.35 where $c_s$ is the velocity of sound and n is the index of refraction), an RF center frequency 50 MHz, f=5 cm, and $\gamma=4°$. The secondary diffraction grating had a ruling of 1200 lines per mm. The group delay produced by this configuration is nonlinear. This nonlinearity can be corrected during a group delay scan by modifying the RF waveform sweep frequency. This can be beneficial when the delay line apparatus is used in OCT systems. In addition, changes in frequency dependent diffraction efficiency can be compensated for by altering the RF signal amplitude. Another difference between the AOM scanning method is that a Doppler shift ($2v_{RF}$) is transferred to the local oscillator signal. This modulation frequency may be removed by using the AOM 28 in a double pass configuration. The AOM configuration is preferable over the mechanical angular scanning configurations because it allows real time (15 kHz) path length scanning with no moving parts.

Figure 20:
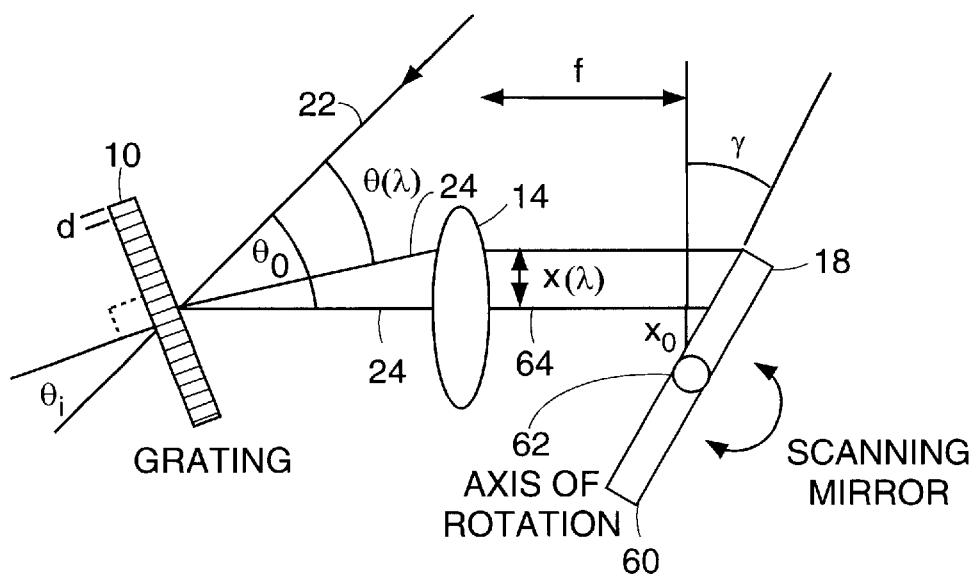
FIG. 20 is a block diagram of a grating based phase control optical delay line using a scanning mirror with its axis of rotation offset from the optical axis.

In order to use the scanning path length delay lines presented in the previous section, the phase delay must be analyzed to determine the heterodyne modulation frequency. Unlike other rapid scanning optical delay lines, such as the linear mechanical translator or the piezoelectric optical fiber stretcher, the change in phase delay using the phase control method is not directly related to the change in group delay. In FIG. 20, the center wavelength is directed towards the tilting mirror 18 and is offset from the axis of rotation by $x^0$. If the mirror surface 60 approximately intersects the axis of rotation 62, the phase delay can be written as, $$\phi(\lambda, t) = \frac{4\pi f \gamma t}{\lambda} \left[ \theta_0 - \arcsin\left(\frac{\lambda}{d} - \sin(\theta_i)\right) + \frac{x_0}{f} \right], \qquad (16)$$

which is a modification of equation. (8) that incorporates a lateral offset of the galvanometer.

The heterodyne modulation frequency for a source with a Gaussian spectral distribution, is determined by the phase shift at the center wavelength, $$\phi(\lambda,t)|_{\lambda_0}. \qquad (17)$$

The phase shift for the scanning mirror configuration with a linear change in angle as a function of time, $\gamma t$, is then $$\phi(\lambda_0, t) = \frac{4\pi\gamma t x_0}{\lambda_0}, \qquad (18)$$

because for this case, $$\theta_0 = \arcsin\left(\frac{\lambda}{d} - \sin(\theta_i)\right). \qquad (19)$$

Thus, the envelope of the autocorrelation function produced by the scanning linear group delay is modulated by a sinusoid, $$\cos(2\pi f_p t), \qquad (20)$$

where the modulation frequency, $$f_p = \frac{2\gamma x_0}{\lambda_0}. \qquad (21)$$

As can be seen by equation (18), if the center wavelength of the spectrum is incident on the mirror axis of rotation ($x^0=0$), no modulation frequency is applied to the local oscillator, even though a scanning linear group delay is produced. Thus, the interferometric signal consists of the envelope of the autocorrelation function without any modulation. This can be useful for OCT imaging systems that perform homodyne detection. This feature of the tilting mirror configuration can be advantageous. If an independent phase modulation is applied to the local oscillator, the system would be capable of scanning at different speeds without changing the center frequency of the band pass filter before demodulation. A phase diversity homodyne detection system would be useful for OCT in this instance.

Furthermore, by translating the scanning mirror 18 so that the center wavelength is offset from the axis of rotation ($x^0 \neq 0$), an arbitrary modulation frequency can be applied to the local oscillator. This feature allows complete control over the center frequency of the local oscillator. The modulation frequency (i.e., phase delay) may be varied by simply translating the tilting mirror 18 perpendicular to the optical axis 64 of the beam. The range of center modulation frequencies that may be achieved is only limited by spectral vignetting due to the finite size of the scanning mirror 18.

Figure 21:
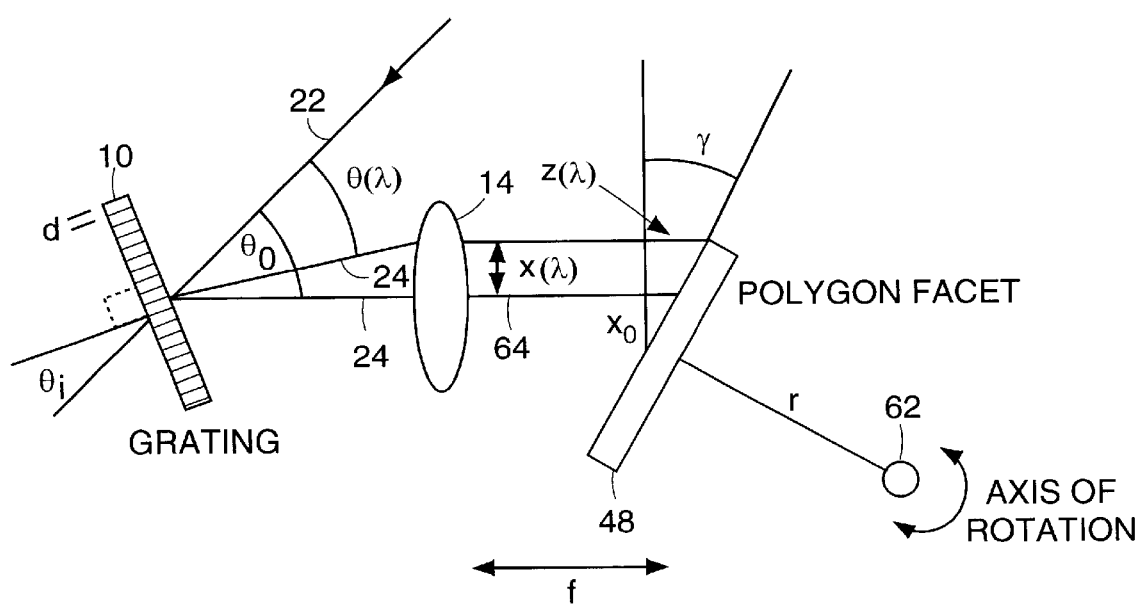
FIG. 21 is a block diagram of a grating based phase control optical delay line using a polygon mirror with its axis of rotation offset from the optical axis.

To this simple approximation, the group-phase delay independence of the phase control apparatus is an advantage for scanning mirrors 18 with an axis of rotation 62 that intersects the mirror surface 60. When the mirror surface 60 is separated from the axis of rotation 62 by a distance, r, however, the group-delay and phase-delay properties are more complex. To an approximation, the group-delay is linear in angle but not in phase delay. For real time OCT applications (>1 kHz), a polygon mirror 46 is the optimal scanning device for rapidly changing the angle, γ (FIG. 21). In this case, to a first order approximation, $x^0$ changes across a single scan, $$x_0(t) = r \tan[(\Omega - \Omega_0)t], \quad (22)$$

where $\Omega$ is the rotation angle and $\Omega_0$ is the angle at which the center wavelength of the source is coincident with the center of the polygon mirror facet. In the limit of small $\Omega - \Omega^0$, $x_0$ is a linear function of t. The modulation frequency in this case becomes, $$f_p(t) = \frac{2r(\Omega - \Omega_0)t}{\lambda_0}. \quad (23)$$

While the change in group delay produced by the polygon scanning mirror 46 is linear, the change in phase is quadratic as a function of time. Since the modulation frequency shifts linearly over the scan, the polygon scanning mirror 46 cannot be used in conjunction with a demodulation method that incorporates a fixed band pass filter. This is an unfortunate result because the polygon scanning mirror 46 is the best mechanical means for obtaining high speed (>1 kHz) linear group delays. The varying modulation frequency can be overcome, however, by using an alternative demodulation scheme, such as adaptive frequency mixing detection, where the frequency at which the demodulation is performed is varied to track the variation in the modulation frequency. This scheme is particularly well suited for OCT imaging applications.

Alternative phase control configurations, such as scanning the grating angle of incidence $\theta_i$ or the grating ruling density, also produce a nonlinear phase delay. By evaluating equation. (8) at $\lambda_0$ for these scanning methods, the phase shift becomes $$\phi(t) = \frac{4\pi f \gamma}{\lambda_0} \left[ \theta_{i0} - \arcsin\left(\frac{\lambda_0}{d(t)} - \sin(\theta_i(t))\right) \right]. \quad (24)$$

As with the polygon scanning mirror 46, the phase is a nonlinear function of time and again, these methods can only be used in conjunction with an adaptive frequency mixing demodulation scheme for OCT imaging applications. Based on the phase produced by the polygon scanner 46, scanning the grating angle of incidence $\theta_i$, and the grating ruling density, it is clear that a change in the demodulation method is warranted to exploit the full potential of the phase control paradigm. Moreover, a Doppler tracking or adaptive frequency mixing detection method which tracks the changing IF heterodyne frequency is useful, especially for OCT imaging systems.

Typical operating parameters for one embodiment of the phase control optical delay are given in terms of an experimental example. Scanning the angle, γ, with a galvanometer produces a linear optical group delay scan with a constant modulation frequency. Because the demodulation electronics used in this study required a constant modulation frequency, a folded double passed scanning mirror configuration was used to perform coherence gating in the high speed OCT system.

A self-phase modulated Kerr Lens Modelocked Cr4+:Forsterite laser was used as the source of low coherence light for the high speed OCT system. The laser was set to an output power of 30 mW. After being transmitted by the fiber optic beamsplitter, the sample arm power was 12 mW. The FWHM spectrum of the source was 75 nm, corresponding to a Gaussian autocorrelation FWHM of 10 μm. The center of the beam was offset on the scanning mirror 18 to produce a modulation frequency of 750 kHz. The FWHM bandwidth of the signal was approximately 350 kHz. This modulation frequency was chosen to enable band pass filtering of the interferometric signal without accepting any contributions from low frequency noise. In order to produce linear angular scans at 1 kHz, the mirror size was minimized to a width of 6 mm. Because of this constraint, the full bandwidth of the self-phase modulated source was not used. If the entire spectrum was employed (200 nm), one side of the spectrum would have been clipped by the edges of the scanning mirror.

The galvanometer was driven with a 1 kHz triangle waveform, enabling 2000 scans per second, twice the speed of the PZT-based high speed OCT system. This rapid scanning rate enabled image acquisition at 4 frames per second for an image size of 512 (lateral)×256 (axial) pixels or 8 frames per second for an image size of 256 (lateral)×256 (axial) pixels. The phase control method produced axial scans that were not corrupted by dropout artifacts due to hysteresis. The total galvanometer scan angle of 3° provided an optical path length delay of 3 mm.

What is claimed is:

1. An optical delay line apparatus, comprising:
   an optical input;
   an optical output; and
   a plurality of optical elements in optical communication with each other,
   wherein said plurality of optical elements guide an optical signal having an optical spectrum from said optical input to said optical output,
   wherein at least one of said plurality of optical elements is a dispersive element which is capable of spatially dispersing the optical spectrum of the optical signal to provide a spatially dispersed optical signal, and wherein at least one of said plurality of optical elements is adjustable to repetitively scan at least one of the phase delay and the group delay of the optical signal between said optical input and said optical output.

2. The optical delay line apparatus of claim 1, further comprising an optical imaging module and a reflective element, each in optical communication with said dispersive element, wherein said dispersive element generates an angularly dispersed optical signal having spectral components, said optical imaging module produces an image of the angularly dispersed optical signal at said reflective element, said reflective element rotates about an axis which is displaceable from a central wavelength of the image to adjust the phase delay, and the angle of said reflective element is alterable to adjust the group delay.

3. The optical delay line apparatus of claim 1, wherein said dispersive element is a diffraction grating and wherein the group delay is adjustable by altering the relative angle between the diffraction grating normal and the incident light beam.

4. The optical delay line apparatus of claim 1, wherein said dispersive element has a spatially periodic structure which spatially disperses wavelength components of the optical spectrum of the optical signal and wherein the group delay is adjusted by altering the spatially periodic structure of said dispersive element.

5. The optical delay line apparatus of claim 1, wherein said dispersive element comprises an acousto-optic modulator having an adjustable spatially periodic structure which varies in response to a radio frequency drive waveform received by said acousto-optic modulator.

6. The optical delay line apparatus of claim 5, wherein said radio frequency drive waveform is repetitively altered to produce a repetitive and substantially constant rate of change of the group delay.

7. The optical delay line apparatus of claim 5, wherein said radio frequency drive waveform is repetitively altered to produce a repetitive change in group delay with a substantially constant optical throughput efficiency.

8. The optical delay line apparatus of claim 5, wherein another of said plurality of optical elements is a double-pass mirror positioned to receive said spatially dispersed optical signal.

9. The optical delay line apparatus of claim 1, wherein said delay line has the property that upon interferometrically combining the optical signal transmitted through said optical delay line with a portion of the optical signal not transmitted through said delay line, a non-zero frequency heterodyne signal is achieved.

10. The optical delay line apparatus of claim 1, wherein at least one of said plurality of optical elements is adjustable to independently affect the phase delay and the group delay of optical signal.

\* \* \* \* \*